US006623647B2

(12) United States Patent
Martin (10) Patent No.: US 6,623,647 B2
(45) Date of Patent: *Sep. 23, 2003

(54) METHODS OF OPTIMIZED CONTROL OF MULTIPLE OXIDIZER FEEDSTREAMS

(75) Inventor: Roy Martin, Downers Grove, IL (US)

(73) Assignee: United States Filter Corporation, Palm Desert, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/098,817

(22) Filed: Mar. 15, 2002

(65) Prior Publication Data

US 2002/0153325 A1 Oct. 24, 2002

Related U.S. Application Data

(62) Division of application No. 09/780,198, filed on Feb. 9, 2001.

(51) Int. Cl.$^7$ ................................................. C02F 1/00
(52) U.S. Cl. ................ 210/742; 205/778.5; 205/779.5; 210/743; 210/746; 210/754; 210/755; 210/756; 210/758; 210/759; 210/764
(58) Field of Search ............................... 205/743, 778.5, 205/779.5; 204/406, 408, 415; 210/742, 743, 746, 752, 754, 755, 756, 758, 759, 764; 702/22, 23, 25, 27, 32, FOR 115–118

(56) References Cited

U.S. PATENT DOCUMENTS

| | | |
|---|---|---|
| 2,008,684 A | 7/1935 | Craddock |
| 2,212,260 A | 8/1940 | Brothman |
| 2,249,263 A | 7/1941 | Wheelwright, Jr. |
| 2,268,461 A | 12/1941 | Nichols |
| 2,556,014 A | 6/1951 | Tolman |
| 2,651,582 A | 9/1953 | Courtney |
| 2,686,110 A | 8/1954 | Carver |

(List continued on next page.)

FOREIGN PATENT DOCUMENTS

| | | |
|---|---|---|
| DE | 262 139 A3 | 11/1988 |
| DE | 4 312 417 A1 | 10/1994 |
| EP | 0 257 740 | 2/1988 |
| EP | 0 504 621 A1 | 9/1992 |
| FR | 2672058 A1 | 7/1992 |
| GB | 2 335 044 A | 9/1999 |
| JP | 11028479 | 2/1999 |
| JP | 2000-221165 A | 8/2000 |
| LU | 80951 | 2/1979 |
| WO | 89/08728 A1 | 9/1989 |
| WO | 96/30307 A1 | 10/1996 |
| WO | 99/24369 A | 5/1999 |
| WO | 00/34760 A1 | 6/2000 |
| WO | 01/98558 A2 | 12/2001 |

OTHER PUBLICATIONS

Dexter et al., "Use and Limitations of Electrochemical Techniques for Investigating Microbiological Corrosion", Corrosion, 1991, vol. 47, No. 4, pp. 308–318.

Gusmano et al., "Electrochemical Noise Resistance as a Tool for Corrosion Rate Prediction", Corrosion, 1997, vol. 53, No. 11, pp. 860–868.

Kim, Yong H., "On the Activation of Polymeric Flocculants," AIChE Annual Spring Meeting, Houston, TX, Apr. 2–6, 1989.

U.S. Filter/Stranco, "Ryznar Stability Index The 3$^{rd}$ Dimension Needed for Proper 'Water Balance,'" Aquatic Technology Newsletter, vol. 1, No. 1, pp. 1–3.

(List continued on next page.)

Primary Examiner—Peter A. Hruskoci
(74) Attorney, Agent, or Firm—Wolf, Greenfield & Sacks, P.C.

(57) ABSTRACT

This invention is directed to a method and apparatus for controlling and optimizing the feed of two or more oxidizers to an aqueous stream, thereby providing a synergistic effect. The system combines the use of amperometric or ORP based sensor technology with amperometric sensor technology employing a gas permeable membrane, thereby providing definitive control of each oxidizer feed stream.

15 Claims, 3 Drawing Sheets

U.S. PATENT DOCUMENTS

| | | |
|---|---|---|
| 2,740,696 A | 4/1956 | Longwell |
| 3,252,689 A | 5/1966 | Blomgren, Sr. et al. |
| 3,319,937 A | 5/1967 | Wilson et al. |
| 3,389,970 A | 6/1968 | Scheibel |
| 3,536,646 A | 10/1970 | Hatch et al. |
| 3,559,959 A | 2/1971 | Davis et al. |
| T896,051 I4 | 3/1972 | Hamlin et al. |
| 3,702,298 A | 11/1972 | Zsoldos et al. |
| 3,742,735 A | 7/1973 | Verreyne et al. |
| 3,747,899 A | 7/1973 | Latinen et al. |
| 3,756,570 A | 9/1973 | Bühner |
| 3,794,817 A | 2/1974 | Shinskey |
| 3,852,234 A | 12/1974 | Venema |
| 3,965,027 A | 6/1976 | Boffardi et al. |
| 4,016,078 A | 4/1977 | Clark |
| 4,113,688 A | 9/1978 | Pearson |
| 4,125,574 A | 11/1978 | Kastner et al. |
| 4,146,676 A | 3/1979 | Saeman et al. |
| 4,171,166 A | 10/1979 | Trowbridge et al. |
| 4,217,145 A | 8/1980 | Gaddis |
| 4,218,147 A | 8/1980 | Rosenberger |
| 4,233,265 A | 11/1980 | Gasper |
| 4,234,440 A | 11/1980 | Hirozawa et al. |
| 4,241,016 A | 12/1980 | Hirozawa et al. |
| 4,243,636 A | 1/1981 | Shiraki et al. |
| 4,300,909 A | 11/1981 | Krumhansl |
| 4,433,701 A | 2/1984 | Cox et al. |
| 4,470,907 A | 9/1984 | Sencza |
| 4,522,502 A | 6/1985 | Brazelton |
| 4,550,011 A | 10/1985 | McCollum |
| 4,575,678 A | 3/1986 | Hladky |
| 4,581,074 A | 4/1986 | Mankina et al. |
| 4,648,043 A | 3/1987 | O'Leary |
| 4,664,528 A | 5/1987 | Rodgers et al. |
| 4,701,055 A | 10/1987 | Anderson |
| 4,719,252 A | 1/1988 | Dutton et al. |
| 4,747,978 A | 5/1988 | Loehr et al. |
| 4,752,740 A | 6/1988 | Steininger |
| 4,913,822 A | 4/1990 | Chen et al. |
| 4,965,016 A | 10/1990 | Saitoh et al. |
| 4,977,292 A | 12/1990 | Hwa et al. |
| 5,000,866 A | 3/1991 | Woyciesjes |
| 5,004,549 A | 4/1991 | Wood et al. |
| 5,018,871 A | 5/1991 | Brazelton et al. |
| 5,030,334 A | 7/1991 | Hale |
| 5,061,456 A | 10/1991 | Brazelton et al. |
| 5,112,521 A | 5/1992 | Mullins et al. |
| 5,130,033 A | 7/1992 | Thornhill |
| 5,135,968 A | 8/1992 | Brazelton et al. |
| 5,139,627 A | 8/1992 | Eden et al. |
| 5,164,429 A | 11/1992 | Brazelton et al. |
| 5,213,694 A | 5/1993 | Craig |
| 5,239,257 A | 8/1993 | Muller et al. |
| 5,256,307 A | 10/1993 | Bachhofer et al. |
| 5,262,963 A | 11/1993 | Stana et al. |
| 5,306,355 A | 4/1994 | Lagana |
| 5,306,432 A | 4/1994 | Puetz |
| 5,316,031 A | 5/1994 | Brazelton et al. |
| 5,320,748 A | 6/1994 | Dupuis |
| 5,332,511 A | 7/1994 | Gay et al. |
| 5,382,367 A | 1/1995 | Zinkan et al. |
| 5,422,014 A | 6/1995 | Allen et al. |
| 5,424,032 A | 6/1995 | Christensen et al. |
| 5,489,344 A | 2/1996 | Martin et al. |
| 5,494,588 A | 2/1996 | LaZonby |
| 5,575,920 A | 11/1996 | Freese et al. |
| 5,658,467 A | 8/1997 | LaZonby et al. |
| 5,683,654 A | 11/1997 | Dallmier et al. |
| 5,736,097 A | 4/1998 | Ono |
| 5,770,039 A | 6/1998 | Rigney et al. |
| 5,783,092 A | 7/1998 | Brown et al. |
| 5,785,867 A | 7/1998 | LaZonby et al. |
| 5,800,732 A | 9/1998 | Coughlin et al. |
| 5,814,233 A | 9/1998 | Starkey et al. |
| 5,814,247 A | 9/1998 | Derule et al. |
| 5,820,256 A | 10/1998 | Morrison |
| 5,849,985 A | 12/1998 | Tieckelmann et al. |
| 5,855,791 A | 1/1999 | Hays et al. |
| 5,858,246 A | 1/1999 | Rafter et al. |
| 5,858,249 A | 1/1999 | Higby |
| 5,866,013 A | 2/1999 | Kessler et al. |
| 5,882,526 A | 3/1999 | Brown et al. |
| 5,888,374 A | 3/1999 | Pope et al. |
| 5,895,565 A | 4/1999 | Steininger et al. |
| 5,902,751 A | 5/1999 | Godec et al. |
| 5,947,596 A | 9/1999 | Dowd |
| 5,972,196 A | 10/1999 | Murphy et al. |
| 5,980,758 A | 11/1999 | LaZonby et al. |
| 5,985,155 A | 11/1999 | Maitland |
| 6,015,484 A | 1/2000 | Martinchek et al. |
| 6,030,842 A | 2/2000 | Peachey-Stoner |
| 6,045,706 A | 4/2000 | Morrison et al. |
| 6,068,012 A | 5/2000 | Beardwood et al. |
| 6,106,770 A | 8/2000 | Ohki et al. |
| 6,120,619 A | 9/2000 | Goudiakas et al. |
| 6,120,698 A | 9/2000 | Rounds et al. |
| 6,132,593 A | 10/2000 | Tan |
| 6,143,184 A | 11/2000 | Martin et al. |
| 6,146,538 A | 11/2000 | Martin |
| 6,149,819 A | 11/2000 | Martin et al. |
| 6,159,552 A | 12/2000 | Riman et al. |
| 6,238,555 B1 | 5/2001 | Silveri et al. |
| 6,270,680 B1 * | 8/2001 | Silveri et al. ............... 210/746 |
| 6,284,144 B1 * | 9/2001 | Itzhak ........................ 205/473 |
| 6,315,950 B1 | 11/2001 | Harp et al. |
| 6,409,926 B1 | 6/2002 | Martin |
| 6,419,817 B1 | 7/2002 | Martin |
| 6,423,234 B1 | 7/2002 | Martin |
| 2002/0043650 A1 | 4/2002 | Martin |
| 2002/0152036 A1 | 10/2002 | Martin |

OTHER PUBLICATIONS

U.S. Filter/Stranco, "Total Dissolved Solids, Friend or Foe?", Aquatic Technology Newsletter, vol. 1, No. 2, 1988; pp. 1–7.

U.S. Filter/Stranco, "The Relationship of ORP to PPM and Its Automated Control," Aquatic Technology Newsletter, vol. 1, No. 3, 1999, pp. 1–5.

U.S. Filter/Stranco, "The Chemistry and Control of Chloramines," Aquatic Technology Newsletter, vol. 1, No. 4, 1999, pp. 1–5.

U.S. Filter/Stranco, "Yes, Your Pool Needs Calcium Too," Aquatic Technology Newsletter, vol. 1, No. 5, pp. 1–3.

Carpenter, Colleen et al., "Chlorine Disinfection of Recreational Water for *Cryptosporidium parvum*," *Emerging Infectious Diseases*, vol. 5, No. 4, Jul.–Aug. 1999, pp. 579–584.

U.S. Filter/Stranco, "Why Do I Have Algae In My Pool?" Aquatic Technology Newsletter, vol. 1, No. 6, 1999, pp. 1–2.

Kowalsky, L., "Pool–Spa Operators Handbook," National Swimming Pool Foundation, 1983–1990.

Lynntech, Inc., "Electrochemical Ozone Generator," Model 124 Product Literature (date unknown).

U.S. Filter/Stranco, "Strantrol Automated Water Chemistry Control for Commercial Pools," 1998.

U.S. Filter/Stranco, "Strantrol System 3 Pool & Spa Chemistry Controller," 2000.

U.S. Filter/Stranco, "Strantrol System 4 Pool & Spa Chemistry Controller," 2000.

U.S. Filter/Stranco, "Strantrol System5 F Pool & Spa Chemistry Controller," 2000.

U.S. Filter/Stranco, "Strantrol System6 Pool Chemistry & Filter Backwash Controller," 2000.

U.S. Filter/Stranco, "Strantrol System7 Mechanical Room Controller for Aquatic Facilities," 2000.

Kloberdanz, B., "The Air in There: Enhancing an Indoor Pool Environment," Recreation Management, 2000.

Selvick, E., "Take Control of 'Yo–Yo' Treatment Cycles," International Aquatics, National Trade Publications, Inc., Jul./Aug. 1997.

Frazier, B., "Automation to the Rescue," Aquatics International, May/Jun. 1998.

Batt, T. et al., "The Water Down Under," Parks & Recreation, Nov. 1999.

Krone, D., "Automated Water Chemistry Control at University of Virginia Pools," Facilities Manager, vol. 13, No. 6, Nov./Dec. 1997.

U.S. Filter/Stranco, "Remote Monitoring for Unstaffed Pools," Parks & Recreation, Nov. 1997.

Minton, E., "On the Waterpark," Swimming Pool/Spa Age (date unknown).

U.S. Filter/Stranco, "Environmental Control at Indoor Pool: New ECS System Eliminates Chronic Air Quality Woes For New York School District Pool," Stranco Products Capsule Case History #806, Jul. 1998.

U.S. Filter/Stranco, "Environmental Control at Indoor Pool Complex: New ECS System Optimizes Air & Water Quality at Colorado Recreation Center," Stranco Products Capsule Case History #807, Nov. 1998.

U.S. Filter/Stranco, "Environmental Control at Indoor Pool: Parks District Uses New ECS System to Eliminate Chronic Air Quality Problems at High School Pool," Stranco Products Capsule Case History #808, May 1999.

U.S. Filter/Stranco, "Environmental Control at Indoor Pool: ECS System Optimizes Air & Water Quality at Texas School District Swim Center," Stranco Products Capsule Case History #811, Nov. 1999.

U.S. Filter/Stranco, "Environmental Control at Special Indoor Pool: New ECS System Eliminates Chronic Air Quality Woes in School District Pool & Spa Serving Special Needs Children," Stranco Products Capsule Case History #812, Oct. 1999.

U.S. Filter/Stranco, "Environmental Control at Indoor Pool: ECS System Eliminates Chronic Air Quality Problems at High School and Parks District Indoor Pool Facility," Stranco Products Capsule Case History #813, Jul. 2000.

U.S. Filter/Stranco, "Environmental Control at Indoor Pool: ECS System Optimizes Air & Water Quality at Iowa Recreation Center," Stranco Products Capsule Case History #814, May 2000.

U.S. Filter/Stranco, "Air & Water Quality Control for Indoor Aquatic Facilities," U.S. Filter Corporation, 1998.

U.S. Filter/Stranco, "Strantrol ECS—Environmental Control System (For Pool)," 2000.

U.S. Filter/Stranco, "Abstracts of Strancol ECS Case Histories," (date unknown).

Williams, K., "Aquatic Facility Operator Manual," National Recreation and Park Association, Second Edition, 1995.

Normenausschusse Wasserwesen, "Treatment and disinfection of water used in bathing facilities," DIN 19643–4, Feb. 1999.

Normenausschusse Wasserwesen, "Treatment and disinfection of water used in bathing facilities," DIN 19643–3, Apr. 1997.

Normenausschusse Wasserwesen, "Treatment and disinfection of water used in bathing facilities," DIN 19643–2, Apr. 1997.

Normenausschusse Wasserwesen, "Treatment and disinfection of water used in bathing facilities," DIN 19643–1, Apr. 1997.

Stranco, "The Best of Poolfax," The Poolfax Newsletter, 1981–1984.

Victorin et al., "Redox potential measurements for determining the disinfecting power of chlorinated water," J. Hyg., Camb., 70, 1972, pp. 313–323.

U.S. Filter/Stranco, "Environmental Control System Training Meeting, Mar. 15, 2000".

Kim, Yong H., "Evaluation of Redox Potential and Chlorine Residual as a Measure of Water Disinfection," presented at the 54th International Water Conference, Pittsburgh, PA, Oct. 11–13, 1993.

Scully et al., Disinfection Interference in Wastewaters by Natural Organic Nitrogen Compounds, Environ. Sci. Techn., vol. 30, No. 5, 1996, pp. 1465–1471.

White, Geor. Clifford, Handbook of Chlorination and Alternative Disinfectants, Third Edition, (date unknown), pp. 803–809, 922–924.

Carlson, S., "Fundamentals of water disinfection," J Water SRT—Aqua, vol. 40, No. 6, (1991), pp. 346–356.

Lund, E., "Oxidative Inactivation of Poliovirus," from the Virological Laboratory of the Department of Bacteriology, University of Gothenburg, and the Virological Department of the Municipal Laboratories, Gothenburg, Sweden, Springer–Verlag, (1963), pp. 1–49.

Lund et al., "The Effect of Oxidation and Reduction on the Infectivity of Poliomyelitis Virus," from the Virological Laboratory of the Department of Bacteriology, University of Gothenburg, and the Virological Department of the Municipal Laboratories, Gothenburg, Sweden, Springer–Verlag, (1961), pp. 100–110.

Lund, E., "Inactivation of Poliomyelitis Virus by Chlorination at Different Oxidation Potentials," from the Virological Laboratory of the Department of Bacteriology, University of Gothenburg, and the Virological Department of the Municipal Laboratories, Gothenburg, Sweden, Springer–Verlag, (1961), pp. 330–342.

Lund, E., "the Significance of Oxidation in Chemical Inactivation of Poliovirus," from the Virological Laboratory of the Department of Bacteriology, University of Gothenburg, and the Virological Department of the Municipal Laboratories, Gothenburg, Sweden, Springer–Verlag, (1963), pp. 1–13.

Lund, E., "The Rate of Oxidative Inactivation of Poliovirus and its Dependence on the Concentration of the Reactants," from the Virological Laboratory of the Department of Bacteriology, University of Gothenburg, and the Virological Department of the Municipal Laboratories, Gothenburg, Sweden, Springer–Verlag, (1963), pp. 1–18.

Stranco, "Solutions: Effluent Dechlorination", Stranco Product Literature (date unknown).

Hensley, R. et al., "Disinfection Metamorphosis: From Chemicals to Control,"Operations Forum, vol. 12, No. 4, Apr. 1995.

Hetzler, J.T. et al., "ORP: A Key to Nutrient Removal," Operations Forum, vol. 12, No. 2, Feb. 1995.

Bossard, G. et al., "Optimizing Chlorination/Dechlorination at a Wastewater Treatment Plant," reprinted from *Public Works,* Jan. 1995.

Eddington, Gordon, "Successfully Managing Wastewater Chlorination," Stranco Product Literature (date unknown).

Ryan, D. et al., "Waste Not, Want Not: Avoiding Chemical Excesses," reprinted from *Operations Forum,* vol. 11, No. 4, Apr. 1994.

D'Adam, D. et al., "A Case Study of Wastewater Plant Disinfection," reprinted from *Public Works Magazine,* Nov. 1994.

"Louisiana Plant Uses New Technology for Dechlorination," reprinted from *American City & County,* Feb. 1994.

Kiser, P. et al., "ORP or Residual: Which Measures Oxidation?" Sep. 19, 1992, pp. 1–7.

"Aquasol Controllers: Chemical Automation for Pools and Spas," Product Literature (date unknown).

"Pool and Spa Controller: Acu–200 Pool Management Software," Product Literature (date unknown).

"Acu–Trol Programmable Controllers," Product Literature from www.acu–trol.com, printed Nov. 19, 1999.

Santa Barbara Control Systems, "Chemtrol™ Programmable Controllers: Integrated Water Treatment with Remote Control," Product Literature, (date unknown).

"Chemtrol Automatic Pool Controllers," Product Literature from www.sbcontrol.com, printed Nov. 19, 1999.

"Chemtrol—PC6000 Controller," Product Literature from www.sbcontrol.com, printed Nov. 19, 1999.

"Chemtrol—PC3000 Controller," Product Literature from www.sbcontrol.com, printed Nov. 19, 1999.

"AK100 Swimming Pool Control Systems," Product Literature from www.acu–trol.com, printed Nov. 19, 1999.

ACU–TROL, "AK100 Series" Product Literature (date unknown).

ACU–TROL, "Acu–Trol Programmable Controllers: AK100 Series and AK200," Product Literature (date unknown).

Aquasol Controllers, Inc., "Aquasol WTC," Product Literature, (date unknown).

Aquasol Controllers, Inc., "What is a Controller?" Product Literature from www.aquasol.com, printed Nov. 19, 1999.

Aquasol Controllers, Inc., "Aquasol WTC Specifications," Product Literature from www.aquasol.com, printed Nov. 19, 1999.

Aquasol Controllers, Inc., "Aquasol SPC Specifications," Product Literature from www.aquasol.com, printed Nov. 19, 1999.

ACU–TROL, "AK100 Summary," Product Literature from www.acu–trol.com, printed Nov. 19, 1999.

Cat Controllers, "CAT 2000+ Programmable Water Chemistry Controller," Product Literature (date unknown).

Rola–Chem Corporation, "The New Wave in Water Management: Take Control with Rola–Chem," Product Catalog, Apr. 1999.

Strand, R. et al., "ORP As a Measure of Evaluating and Controlling Disinfection in Potable Water," (Source and date unknown).

Mansfeld et al., "Electrochemical Noise Analysis of Iron Exposed to NaCl Solutions of Different Corrosivity," *J. Electrochem. Soc.,* vol. 141, No. 5, May 1994, pp. 1402–1404.

Brusamarello et al., "Analysis of Different Methods to Calculate Electrochemical Noise Resistance Using a Three–Electrode Cell," *Corrosion,* vol. 56, No. 3, Mar. 2000, pp. 273–282.

Mansfeld et al., "Electrochemical Noise Analysis of Iron Exposed to NaCl Solutions of Different Corrosivity," *J. Electrochem Soc.,* vol. 140, No. 8, Aug. 1993, pp. 2205–2209.

* cited by examiner

FIG. 3

METHODS OF OPTIMIZED CONTROL OF MULTIPLE OXIDIZER FEEDSTREAMS

RELATED APPLICATIONS

This application is a divisional application, under 37 C.F.R. §1.53(b), of application Ser. No. 09/780,198, filed Feb. 9, 2001.

FIELD OF THE INVENTION

This invention relates to the control of multiple oxidizer levels in water treatment processes, and particularly relates to the use of a combination of sensors including at least one amperometric sensor isolated by a gas permeable membrane.

BACKGROUND OF THE INVENTION

In the areas of both pool water and waste water treatment, there has been an increased trend toward combining oxidizers to achieve a synergistic effect, thereby exceeding the performance of the individual oxidizers. Although there is no question as to the benefits provided by the use of synergistic oxidizer chemistry, the ability to control their concentrations, ratios, and optimize their feed rate in real world applications has proven to be a difficult task. This often leads to overfeeding to ensure adequate results.

Most oxidizer feed applications incorporate either ORP (Oxidation Reduction Potential) or wet chemistry methods which use color change reagents,. e.g. DPD, to indicate the presence and concentration of the oxidizer. ORP has become increasing popular due to its ability to control the feed of oxidizer based on the oxidizer demand.

In many water treatment applications the demand for oxidizer can change over time. In pools for example, as bathers enter the pool water, organic contaminants are introduced to the water that impose a demand on the oxidizer (usually chlorine). In order to maintain the same oxidation potential, the ORP controller would increase the concentration of chlorine in the water. This process ensures enough oxidizer has been added to not only satisfy the organic demand, but also to ensure sufficient residual oxidizer is available to effectively sanitize the water.

In the pool example, chlorine is the sanitizer and therefore must be maintained in sufficient concentrations to effectively provide for a safe bathing environment. However, if another oxidizer is added to the pool water to enhance oxidation of organic contaminants, the ORP based control system can be compromised since either chlorine or the second oxidizer can satisfy the ORP setting.

Should chlorine feed be compromised, the second oxidizer could be fed in sufficient concentrations to meet the ORP set-point. In this instance, sanitation of the water could be compromised. Also, because chlorine concentrations are reduced, the synergistic effects provided by the combined effect of the two oxidizers would also be compromised.

DESCRIPTION OF THE PRIOR ART

U.S. Pat. No. 5,239,257 to Muller et al teaches an amperometric probe with a gas permeable membrane. The patent fails to teach or disclose a measuring system for controlling oxidizers in a water treatment process by combining multiple sensors inclusive of at least one gas permeable membrane enclosed amperometric sensor.

U.S. Pat. No. 5,902,751 to Godec et al teaches a method for the measurement of dissolved carbon employing a gas permeable membrane dividing deionized water from the oxidized sample water and a pair of micro-conductivity and temperature sensors.

U.S. Pat. No. 6,030,842 to Peachey-Stoner teaches a method for determining free halogens in aqueous fluids utilizing an azine indicator material and a benzidine type catalyst material impregnated into a matrix carrier.

The prior art fails to teach or suggest a system for determining and controlling the amounts of free oxidizer in a multiple oxidizer system.

SUMMARY OF THE INVENTION

Many water treatment applications incorporate two oxidizers that together provide a synergistic effect. For example, Advanced Oxidation Technologies (AOTs) can employ ozone with peroxide to produce hydroxyl free radicals (hydroxyl radicals). In yet another similar application, hydrogen peroxide is converted to hydroxyl free radicals using ultra violet radiation. While one oxidizer is predominant, the production of hydroxyl radicals makes for a two-oxidizer application. There are other similar processes used in AOTs with the results being to produce hydroxyl free radicals.

In yet another water treatment application, a halogen based oxidizer such as chlorine is used in combination with peroxygen based oxidizers such as potassium monopersulfate to effectively eliminate the formation of volatile halogenated nitrogen based compounds into the air of indoor aquatic facilities. In this application, both chlorine and monopersulfate are fed to the pool water based on ORP based control.

Although these applications take advantage of the synergistic properties which flow from the use of two oxidizers, they nevertheless fail to optimize the control and/or optimize the feed or production of each oxidizer based, on program performance, e.g. oxidizer demand.

For example in the pool, while ORP initiates oxidizer feed based on demand for the oxidizer(s), this method of control does not clearly differentiate between the oxidizers. Oxidizers are fed proportional to one another. Using this control scheme, dynamic optimization of oxidizer ratios, and verification of individual oxidizer feed is not possible. Similar inefficiencies exist with AOTs.

Accordingly, it is an objective of the instant invention to teach a method of operation and apparatus for performing the method which combines the use of either ORP or amperometric sensor technology, along with at least one amperometric sensor that employs a gas permeable membrane to provide superior process control in two oxidizer systems. The gas permeable membrane described in this application will have the ability to allow gases and/or nonionic compounds to permeate while restricting ionic particles from permeating.

It is a further objective of the instant invention to teach a process wherein the combination of sensor technologies can, in many two oxidizer applications, independently control the oxidizers, verify concentration or presence of both oxidizers, and enhance the optimization of oxidizer(s) feed rates in dynamic systems.

Other objectives and advantages of this invention will become apparent from the following description taken in conjunction with the accompanying drawings wherein are set forth, by way of illustration and example, certain embodiments of this invention. The drawings constitute a part of this specification and include exemplary embodi-

DETAILED DESCRIPTION OF THE INVENTION

In the application employing a halogen-based oxidizer with a peroxygen-based oxidizer, the invention is comprised of at least one amperometric sensor incorporating a gas permeable membrane in conjunction with one or more of ORP, pH, and temperature sensor technologies. These sensors serve as data inputs to a microprocessor or analog based computer. The computer employs some mode of control utilizing Time Based Proportional (TBP), Proportional (P), Proportional Integral (PI), Proportional Integral Differential (PID) and/or on/off control for controlling chemical(s) feed.

To further improve control, the computer can be programmed utilizing either Fuzzy logic or Boolean logic protocols to provide the system with the ability to make changes to various settings or feed adjustments based on evaluation of input data.

In yet another application of the invention, AOT applications employ at least one amperometric sensor utilizing a gas permeable membrane that separates the amperometric electrode from the treated water, along with one or more standard amperometric sensors (no gas permeable membrane). These sensors serve as data inputs to a microprocessor or analog based computer. The computer employs some mode of control utilizing Time Based Proportional (TBP), Proportional Integral (PI), Proportional Integral Differential (PID) and/or on/off control for controlling chemical feed.

To further improve control, the computer can be programmed utilizing Fuzzy logic or Boolean logic to make changes to various settings or feed adjustments based on evaluation of input data.

Halogen/Peroxygen Test

In this test, chlorine in the form of sodium hypochlorite was used in combination with potassium monopersulfate.

The amperometric sensor incorporated a gas permeable membrane used to prevent dissolved solids from influencing the amperometric sensor. Therefore, only dissolved chlorine in the form of hypochlorous acid can permeate the membrane and influence the amperometric sensor. The sensor was calibrated for use with chlorine. The amperometric sensor and supporting hardware employ pH and temperature inputs for accurate determination of free chlorine. An ORP sensor was incorporated to measure water ORP values.

Figure 1:
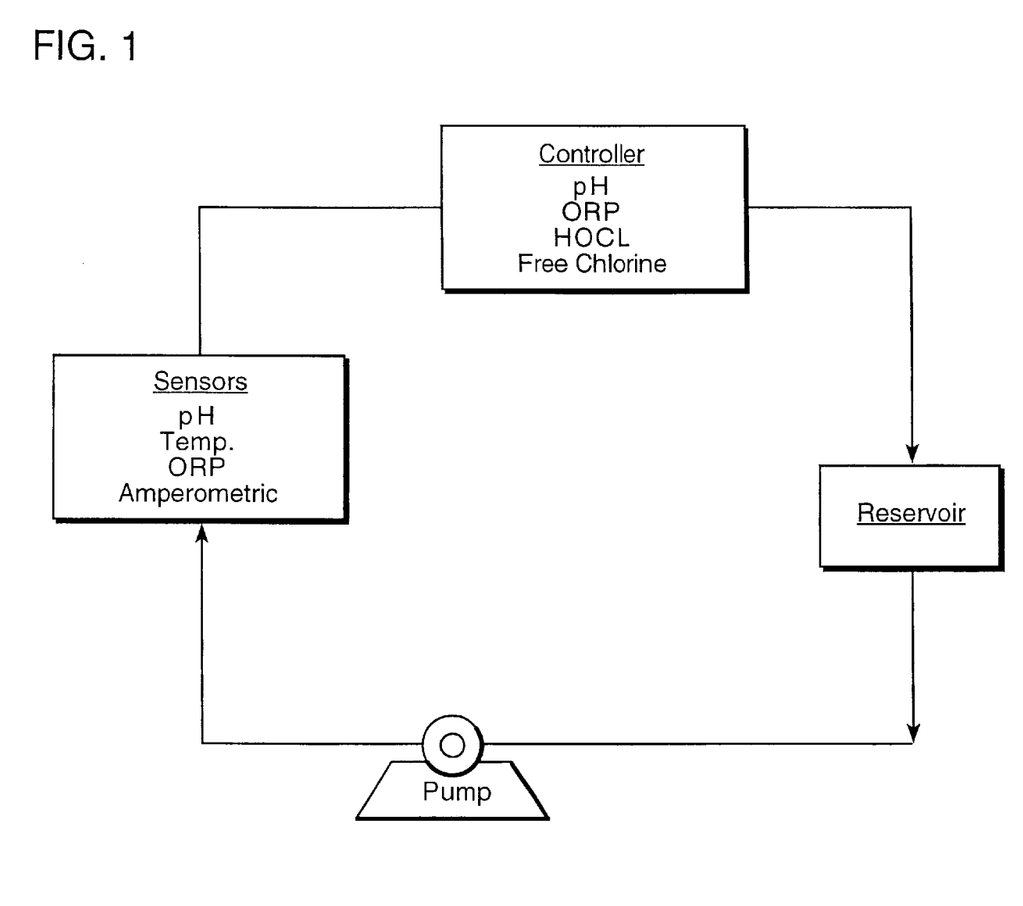
FIG. 1 is a block diagram and flow-sheet of a typical testing device in accordance with the present invention.

A circulating system with a 10-gallon reservoir was used for testing purposes (FIG. 1).

The circulating pump was turned on, the water was treated with sodium bypochlorite, and the pH was adjusted. Free chlorine concentration was verified using standard DPD methods with a HACH DR-2000 spectrophotometer. The amperometric controller was standardized, then allowed to track while samples where periodically tested using DPD free chlorine test. The solution ORP was recorded periodically throughout the test period.

After ensuring the sensors had achieved equilibrium (stabilized readings), the solution was treated with various concentrations of potassium monopersulfate by addition into the top reservoir. After each addition of monopersulfate, the effect on both the amperometric reading and ORP reading were measured and recorded (Table 1).

TABLE 1

| Persulfate Addition (ppm) | Approx. Time lapsed (minutes) | ORP mv | pH | HACH Free Chlorine (ppm) | Amperometric HOCl (ppm) | Amperometric Free Chlorine (ppm) |
|---|---|---|---|---|---|---|
| 0 | 0 | 53 | 0.3 | 5.2 | 2.77 | 5.2 |
| 9 | 5 | 62 | 0.3 | n/a | 2.78 | 5.2 |
| 9 | 15 | 64 | 0.3 | n/a | 2.83 | 5.2 |
| 26 | 30 | 70 | 0.2 | n/a | 2.9 | 5.1 |
| 26 | 50 | 82 | 0.1 | 5.1 | 2.95 | 5.1 |

Figure 2:
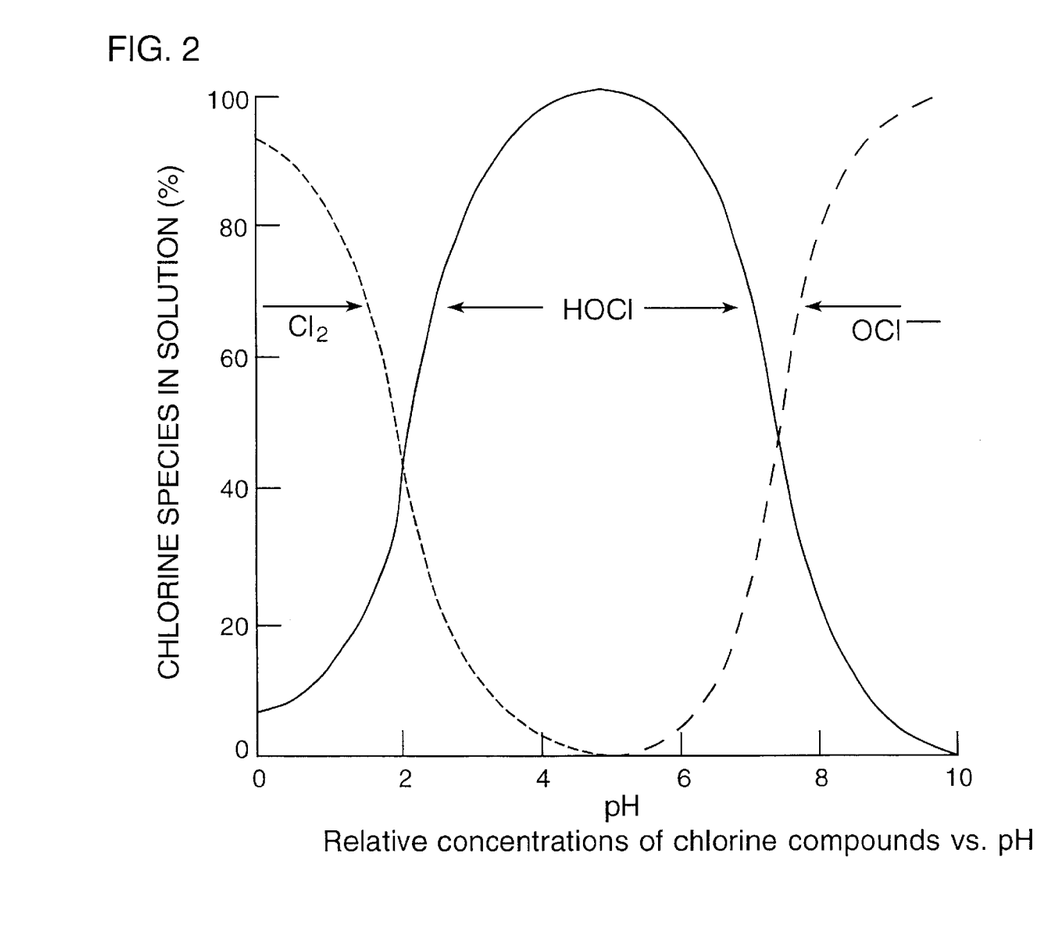
FIG. 2 is a graphical analysis of the relative concentration of chlorine versus pH.

With the addition of the acid based monopersulfate, slight changes in pH induced a change in the measured hypochlorous acid (FIG. 2). However, the calculated free chlorine value remained stable since the monopersulfate exists as an ionized salt that cannot permeate the gas permeable membrane.

It is evident from the results of this test that free chlorine concentration was accurately measured by the amperometric sensor while the ORP value was significantly influenced by the presence of the second oxidizer (potassium monopersulfate). Even with concentrations of monopersulfate magnitudes higher than that applied in actual application such as the pool example, free chlorine residual was accurately measured by the amperometric sensor.

By incorporating this sensor technology into this dual oxidizer application, verification and optimization of chlorine feed would be achieved even in the presence of the second oxidizer. Therefore, in a pool application where chlorine is used as the sanitizer, implementation of this control technology would ensure that low levels of chlorine would not occur due to the satisfied ORP value measured by the ORP controller.

Yet another benefit of this invention is the improved performance achieved through the optimized proportioning of the oxidizer. For instance, if sufficient chlorine is available to ensure sanitation and support its role in the oxidation processes, the second oxidizer could be selected and fed independent of the chlorine. Boolean logic or Fuzzy logic can be effectively included to maximize performance through optimized proportioning of the oxidizers whether fed together or independently.

AOT Test 1

Figure 3:
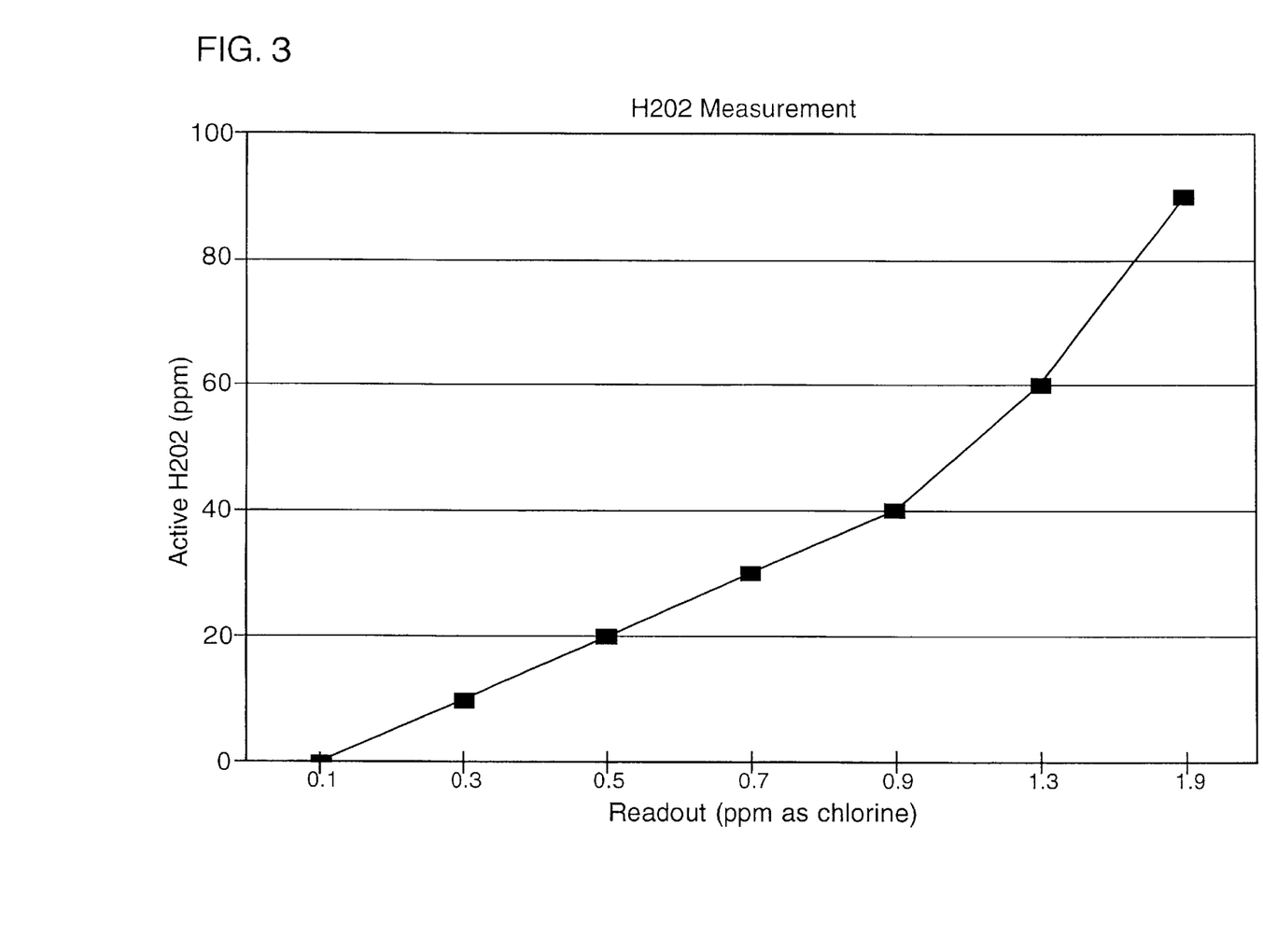
FIG. 3 is a graph of the increase in the amperometric value as Hydrogen peroxide is incrementally added to the solution.

An amperometric sensor combined with a readout display was calibrated to report the measured value of hydrogen peroxide as Chlorine ($Cl_2$). Hydrogen peroxide was incrementally added to the solution. The increase in the amperometric value is illustrated in FIG. 3. Based on these results, it is evident that amperometric technology can effectively detect the presence of hydrogen peroxide.

The same test was performed using an amperometric sensor incorporating a gas permeable membrane. For the 90 ppm active concentration of hydrogen peroxide, the displayed value was 0.1 ppm as $Cl_2$.

Based on these two tests, it is evident the employing these two types of amperometric methods of measure could allow for an accurate measure of oxidizers independently in a two oxidizer environment.

In AOT applications hydrogen peroxide is converted to form hydroxyl free radicals, the second most powerful oxidizer known. This process incorporates combining hydrogen peroxide with ozone, or contacting the hydrogen peroxide with UV radiation.

Hydroxyl free radicals rapidly react with many organic and inorganic contaminants found in many water treatment applications. However, if the concentration of hydroxyl radicals is to be optimized based on demand for the oxidizer, an accurate means of measuring this oxidizer in the presence of the second oxidizer must be employed.

ORP sensors do not provide an accurate method for measuring hydrogen peroxide. Amperometric sensor technology can be applied as previously reviewed. However, hydroxyl radicals can interfere with the amperometric sensor if present with the hydrogen peroxide. In order to adjust the concentration of hydroxyl radicals, independent measure of hydroxyl radicals must be made while in the presence of residual hydrogen peroxide.

Like hypochlorous acid, hydroxyl radicals are nonionic. This enables them to permeate through gas permeable membranes like that employed in the previous test. Hydrogen peroxide on the other hand possesses a strong anionic charge.

An amperometric sensor calibrated to report the oxidizer concentration as chlorine ($Cl_2$) incorporated a gas permeable membrane.

A sample of water was treated with 600 ppm of active hydrogen peroxide by adding 30% laboratory grade hydrogen peroxide to distilled water. A sample of solution was placed on a magnetic stirrer, the sensor with the membrane was immersed into a sample of the solution, the stirrer was activated, and the sensor was allowed to equilibrate for approximately 30-minutes.

Another equal volume of sample was placed in a reaction vessel, in which a UV lamp was placed. The sample with the lamp was periodically immersed in a swirling ice bath to maintain temperature at 23° C. (±1° C.). The solution was exposed for approximately 30 minutes.

After equilibrating for approximately 30 minutes, the amperometric reading was recorded followed by the ORP, and temperature. After recording, the UV sample was given a final ice water bath to stabilize the solution temperature. The lamp was disengaged, and the amperometric w/gas membrane sensor was immersed into the solution. The magnetic stirrer was initiated and the sensor was allowed to equilibrate.

After approximately 60 seconds, the measured value on the display increased significantly and in approximately 3-minutes reached a value of 8.38 as $Cl_2$ as illustrated in the following table. The pH, ORP and temperature were also recorded.

| Sample Name | Temperature ° C. | Amperometric w/membrane | ORP | pH |
|---|---|---|---|---|
| Control | 23 | 0.37 | 245 | 7.25 |
| UV radiated | 23 | 8.38 | 240 | 7.25 |

AOT Test 2

To further demonstrate the ability to differentiate oxidizers and provide superior process control, a 500 ml sample of tap water was treated with 1 ml of 30% hydrogen peroxide. 50 ml of solution was removed and radiated with UV for 30 minutes. The remaining 450 ml of peroxide solution was stirred using a magnetic stirrer with the membrane amperometric sensor immersed.

After 30 minutes and temperature adjustment with an ice bath, the UV radiated solution was reintroduced to the starting 600 ppm solution. Because both solutions began with 600 ppm of active hydrogen peroxide, addition of the solution would not affect the concentration of peroxide and thereby induce interference to the reading. In fact, it is reasonable to assume it would reduce the peroxide concentration since some of the peroxide had been consumed in the production of hydroxyl radicals.

The results clearly demonstrate the membrane-amperometric based technology has the ability to insulate electrode from significant interferences induced by the presence of hydrogen peroxide, thereby allowing effective detection and measurement of hydroxyl radicals.

| Sample Name | Temperature ° C. | Amperometric w/membrane |
|---|---|---|
| Control | 22 | 1.1 |
| Treated | 22 | 8.3 |

Including gas permeable membrane based amperometric technology with conventional amperometric technology provides superior process control of two oxidizers in two oxidizer systems.

One example is to maintain sufficient hydrogen peroxide in a body of water, such as a pool, for sanitation with use of a standard amperometric sensor. Then enhancing oxidation of organics with hydroxyl radicals by applying the gas membrane amperometric sensor technology to measure residual hydroxyl radicals directly, or by difference between the two gas membrane amperometric readings, one taken before and one after hydroxyl radicals are employed. This application could effectively be applied to pools as well as other water treatment applications where oxidation using hydroxyl free radicals would effectively assist in the reduction of organic and other oxidizable inorganic substances.

To further illustrate other potential performance benefits offered by this process control system, with increased concern of cryptosporidium contamination of water, and the high chlorine tolerance of said organisms, the ability to control hydroxyl free radical concentrations offers the ability to destroy the protective lipid layer of the Cryptosporidium Oocyst by inoculating the water with effective doses of hydroxyl free radicals. Application of this technology with additional treatment and/or on-line monitoring could further improve water safety and quality.

The hydroxyl measurement can be used as part of a feedback control by which adjusting the introduction of hydroxyl radicals into the water to be treated, or by increasing the production rate of hydroxyl radicals by increasing or decreasing the ozone concentration or UV intensity and/or contact with the supporting oxidizer (peroxide or ozone) is controlled.

Yet another method of applying this technology to improve the effectiveness and efficiency of 2-oxidizer systems when utilizing a halogen oxidizer is to measure the free halogen concentration with the gas permeable membrane amperometric sensor, while also measuring the solution pH and ORP. An algorithm is used to correlate the concentration of oxidizer demand based on the required free halogen concentration needed to achieve the measured ORP for a given measured pH.

For a given water quality, it will require a specific concentration of free halogen oxidizer at a given pH to achieve a targeted ORP value. This concentration of halogen will not change unless the demand for the oxidizer changes (at a constant pH). If the measured free halogen concentration needed to achieve a targeted ORP increases, the demand in the water has increased. By using an algorithm to identify the presence of this demand, a second oxidizer can be employed to effectively address this demand. For example, the feed rate or production rate of hydroxyl radicals can be adjusted in real-time utilizing this form of control to maximize the performance of the treatment program.

In one or more embodiments the present invention provides a method of treating water involving addition of a halogen donor and a peroxygen compound to the water to maintain the free halogen level of the water at about 0.2 ppm to about 10 ppm and maintain the ORP of the water at about 700 mV to about 850 mV. And, in some embodiments of the present invention, the ORP is maintained at about 750 mV to about 850 mV, preferably, about 760 mV to about 800 mV.

It is to be understood that while a certain form of the invention is illustrated, it is not to be limited to the specific form or arrangement of part herein described and shown. It will be apparent to those skilled in the art that various changes may be made without departing from the scope of the invention and the invention is not to be considered limited to what is shown and described in the specification and drawings.

What is claimed is:

1. A method of treating water in a water system comprising:
    measuring a free halogen level of the water wit an amperometric sensor having a gas permeable membrane and an ORP of the water;
    controlling addition of a halogen donor to the water to maintain the free halogen level at about 0.2 ppm to about 10 ppm in the water based on the measured free halogen level; and
    controlling addition of a peroxygen compound to the water to maintain an ORP of about 700 mV to about 850 mV in the water based on the measured ORP.

2. The method of claim 1, further comprising optimizing the ratio of halogen donor to peroxygen compound to maintain the free halogen level at about 0.2 ppm to about 10 ppm while maintaining the ORP of about 700 mV to about 850 mV in the water.

3. The method of claim 1, further comprising controlling at least one of temperature and pH of the water.

4. The method of claim 1, further comprising maintaining a high oxidation rate in the water to cause any halogenated amine compounds in air to be reabsorbed in the water.

5. The method of claim 1, wherein controlling addition of the halogen donor incorporates any of time-based proportional control, proportional control, proportional-integral control, proportional integral differential, on/off control and combinations thereof.

6. The method of claim 1, wherein controlling addition of the peroxygen compound incorporates any of time-based proportional control, proportional control, proportional-integral control, proportional integral differential, on/off control and combinations thereof.

7. The method of claim 1, wherein the ORP is maintained at about 760 mV to about 800 mV.

8. The method of claim 1, wherein the halogen donor is selected from the group consisting of trichloroisocyanuric acid, dichloroisocyanuric acid, sodium bromide, hydantoin-based bromine, chlorine, calcium hypochlorite, sodium hypochlorite, lithium hypochlorite, and mixtures thereof.

9. The method of claim 1, wherein the peroxygen compound is selected from the group consisting of hydrogen peroxide, sodium peroxide, potassium peroxide, sodium perborate, potassium perborate, sodium monopersulfate, potassium monopersulfate, ammonium monopersulfate, sodium peroxydisulfate, potassium peroxydisulfate, and ammonium peroxydisulfate.

10. A method of facilitating treating water in a water system comprising providing a controller that receives signals from an amperometric sensor having a gain permeable membrane and an ORP sensor and regulates addition to the water of at least one of a halogen donor and a peroxygen compound to maintain a halogen concentration of about 0.2 ppm to about 10 ppm and an ORP of about 700 mv to about 850 mV of the water based on the signals from the amperometric senior and the ORP sensor.

11. A method of treating water in a water system comprising:
    adding a free halogen donor to the water;
    adding a peroxygen compound to the water;
    providing an amperometric sensor having a gas permeable membrane that sends a signal corresponding to a free halogen concentration in the water to a controller;
    providing an ORP sensor that sends a signal corresponding to an ORP of the water to the controller;
    maintaining the free halogen concentration in the water at between about 0.2 ppm and about 10 ppm based on the signal from the amperometric sensor; and
    maintaining the ORP in the water at between about 700 mV and 850 mV based on the signal from the ORP sensor.

12. The method of claim 11, further comprising the step of controlling at least one of a temperature and a pH of the water.

13. The method of claim 11, the ORP is maintained at about 760 mV to about 800 mV.

14. The method of claim 11, wherein the free halogen donor comprises at least one of trichloroisocyanuric acid, dichloroisocyanuric acid, sodium bromide, hydantoin-based bromine, chlorine, calcium hypochlorite, sodium hypochlorite, lithium hypochlorite, and mixtures thereof.

15. The method of claim 11, wherein the peroxygen compound comprises at least one of hydrogen peroxide, sodium peroxide, potassium peroxide, sodium perborate, potassium perborate, sodium monopersulfate, potassium monopersulfate, ammonium monopersulfate, sodium peroxydisulfate, potassium peroxydisulfate, and ammonium peroxydisulfate.

* * * * *